US011754552B2

(12) United States Patent
Sarwal et al.

(10) Patent No.: US 11,754,552 B2
(45) Date of Patent: Sep. 12, 2023

(54) USE OF IMMUNE REPERTOIRE DIVERSITY FOR PREDICTING TRANSPLANT REJECTION

(71) Applicant: The Regents of the University of California, Oakland, CA (US)

(72) Inventors: Minnie Sarwal, San Francisco, CA (US); Marina Sirota, Belmont, CA (US); Silvia Pineda San Juan, Madrid (ES)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1404 days.

(21) Appl. No.: 16/005,602

(22) Filed: Jun. 11, 2018

(65) Prior Publication Data

US 2018/0356403 A1 Dec. 13, 2018

Related U.S. Application Data

(60) Provisional application No. 62/517,584, filed on Jun. 9, 2017.

(51) Int. Cl.
   *C12Q 1/68* (2018.01)
   *G01N 33/50* (2006.01)
   (Continued)

(52) U.S. Cl.
   CPC ....... *G01N 33/5094* (2013.01); *C12Q 1/6851* (2013.01); *C12Q 1/6883* (2013.01);
   (Continued)

(58) Field of Classification Search
   CPC ....................................................... C12Q 1/68
   (Continued)

(56) References Cited

U.S. PATENT DOCUMENTS

| 2016/0002731 A1* | 1/2016 | Robins | C12Q 1/6886 |
| | | | 702/19 |
| 2016/0340729 A1* | 11/2016 | Emerson | C12Q 1/6881 |
| 2019/0169698 A1* | 6/2019 | Faham | C12Q 1/6809 |

FOREIGN PATENT DOCUMENTS

| WO | WO-2014011735 A1 * | 1/2014 | ......... C12N 15/1075 |
| WO | WO-2014144495 A1 * | 9/2014 | ............. C07K 16/00 |

OTHER PUBLICATIONS

Alachkar, H. et al. Quantitative characterization of T-cell repertoire and biomarkers in kidney transplant rejection. BMC Nephrol. 17, 181 (2016).*

(Continued)

*Primary Examiner* — Aaron A Priest
(74) *Attorney, Agent, or Firm* — Kilpatrick Townsend & Stockton LLP

(57) ABSTRACT

Methods of assessing a graft recipient's predisposition to reject a transplant are provided. The risk of transplant rejection may be assessed in a subject prior to transplant, wherein subjects having a greater immune repertoire diversity prior to transplant are more susceptible to transplant rejection. Also, increases in immune repertoire diversity after transplant are indicative of transplant risk after. In another aspect, the presence or elevated abundance of immune elements comprising IGHV3-23 sequences are indicators of transplant rejection risk. In another aspect the scope of the invention encompasses methods of treating transplant rejection in a subject, by assessing transplant risk and administering immunosuppressive therapy in accordance with assessed risk.

7 Claims, 4 Drawing Sheets

(51) Int. Cl.
- C12Q 1/6851 (2018.01)
- G01N 33/564 (2006.01)
- C12Q 1/6883 (2018.01)
- G01N 33/68 (2006.01)
- G16B 5/20 (2019.01)
- G16B 5/00 (2019.01)

(52) U.S. Cl.
CPC ....... *G01N 33/564* (2013.01); *G01N 33/6854* (2013.01); *G16B 5/20* (2019.02); *C12Q 2600/106* (2013.01); *C12Q 2600/158* (2013.01); *C12Q 2600/16* (2013.01); *G01N 33/505* (2013.01); *G01N 33/5052* (2013.01); *G01N 2333/70503* (2013.01); *G01N 2800/245* (2013.01); *G16B 5/00* (2019.02)

(58) Field of Classification Search
USPC ........................................................ 435/6.12
See application file for complete search history.

(56) References Cited

OTHER PUBLICATIONS

Morris, H. et al. Tracking donor-reactive T cells: Evidence for clonal deletion in tolerant kidney transplant patients. Sci. Transl. Med. 7, 272ra10 (2015).*

Dziubianau, M. et al. TCR repertoire analysis by next generation sequencing allows complex differential diagnosis of T cell-related pathology. Am. J. Transplant. 13, 2842-2854 (2013).*

Morris, H. et al. Tracking donor-reactive T cells: Evidence for clonal deletion in tolerant kidney transplant patients. Sci. Transl. Med. 7, (2015).

Palanichamy, A. et al. Immunoglobulin class-switched B cells form an active immune axis between CNS and periphery in multiple sclerosis. Sci. Transl. Med. 6, 248ra106-248ra106 (2014).

Strauli, N. B. & Hernandez, R. D. Statistical inference of a convergent antibody repertoire response to influenza vaccine. Genome Med. 8, 60 (2016).

Roskin, K. M. et al. IgH sequences in common variable immune deficiency reveal altered B cell development and selection. Sci. Transl. Med. 7, 302ra135 (2015).

Massart, A., Ghisdal, L., Abramowicz, M. & Abramowicz, D. Operational tolerance in kidney transplantation and associated biomarkers. Clin. Exp. Immunol. 189, 138-157 (2017).

Beausang, J. F. et al. B cell repertoires in HLA-sensitized kidney transplant candidates undergoing desensitization therapy. J. Transl. Med. 15, 9 (2017).

Ferdman, J. et al. Expansion and somatic hypermutation of B-cell clones in rejected human kidney grafts. Transplantation 98, 766-72 (2014).

Vollmers, C. et al. Monitoring Pharmacologically Induced Immunosuppression by Immune Repertoire Sequencing to Detect Acute Allograft Rejection in Heart Transplant Patients: A Proof-of-Concept Diagnostic Accuracy Study. PLOS Med. 12, e1001890 (2015).

* cited by examiner

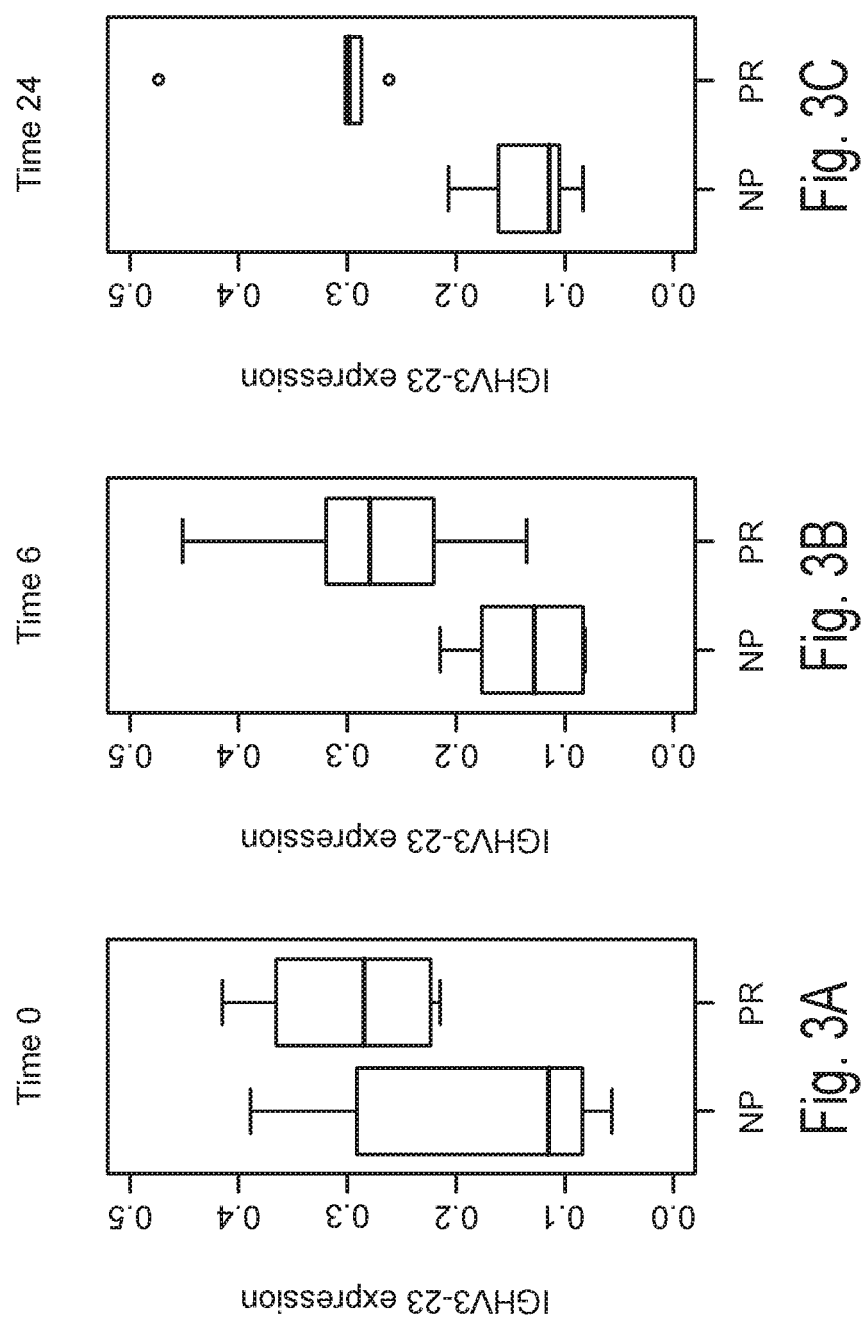

USE OF IMMUNE REPERTOIRE DIVERSITY FOR PREDICTING TRANSPLANT REJECTION

CROSS-REFERENCE TO RELATED APPLICATIONS

This application claims the benefit of priority to U.S. Provisional Application Ser. No. 62/517,584 entitled "Use of Immune Repertoire Diversity For Predicting Transplant Rejection," filed May 5, 2017, the contents which are hereby incorporated by reference.

STATEMENT REGARDING FEDERALLY SPONSORED RESEARCH OR DEVELOPMENT

Funding: This invention was made with government support under grant nos. U01 AI113362, P30 AR070155 and K01 LM012381 awarded by the National Institutes of Health. The government has certain rights in the invention.

BACKGROUND OF THE INVENTION

Transplant rejection is a serious problem affecting a significant portion of transplant recipients. Grafts are susceptible to acute or chronic immune-mediated graft injury, facilitated by cellular and humoral immune effectors. Unfortunately, there are currently no reliable methods for predicting the risk of immune-mediated graft injury, either before transplant or following engraftment of the organ. Accordingly, there is an ongoing need in the art for methods of assessing a transplant recipient's' risk of immune-mediated graft injury.

For example, kidney transplantation (Ktx) is the preferred treatment of end-stage renal disease and chronic kidney disease. Even though there have been significant improvements in tissue matching for donor-recipient HLA antigens, mismatching of other, unknown factors can also drive alloimmune injury with acute and chronic rejection, with resultant poor long-term graft outcomes. Ultimately, around 50% of kidney allografts, with no major HLA-mismatches, are still lost within 10 years of transplantation.

The diversity of the immune response to various immunogenic epitopes is as yet, poorly understood. The role of T-cells in organ transplant rejection has been somewhat explored, and there is increasing appreciation of the additional role of B-cells and antibodies in triggering rejection processes. A key feature of B cells is their enormous diversity. Each individual is capable of producing more than $10^{13}$ different antibodies which enables the subject to recognize a vast array of foreign antigens.

Human B cell receptors (BCRs) and antibodies comprise immunoglobulin proteins (Igs), consisting of two identical heavy-chains (IgH) formed by five isotypes: IgM, IgD, IgA, IgE and IgG and two light-chains. An Ig contains a variable and a constant domain. Antigen binding occurs in the variable domain, which is generated by recombination of a set of variable (V), diversity (D) and joining (J) gene segments forming the B-cell immune repertoire (IR), and its diversity is mainly concentrated in the complementary-determining region 3 (CDR3). During the process of affinity maturation, somatic hypermutation occurs in the variable region. A potent adaptive immune response is reliant upon the expansion of B-cell clones and a process termed affinity maturation, during which somatic mutations are introduced into the Ig gene rearrangements and B-cells with higher affinity for antigen are selected.

The study of the IR in organ transplant is crucial to understand what triggers and sustains the rejection process and how it may eventually accelerate the path towards graft failure. To date, T-cell IR analysis in Ktx has been carried out in very limited numbers of patients, for example, as described in Alachkar, H. et al. Quantitative characterization of T-cell repertoire and biomarkers in kidney transplant rejection. *BMC Nephrol.* 17, 181 (2016); Morris, H. et al. Tracking donor-reactive T cells: Evidence for clonal deletion in tolerant kidney transplant patients. *Sci. Transl. Med.* 7, (2015); and Dziubianau, M. et al. TCR Repertoire Analysis by Next Generation Sequencing Allows Complex Differential Diagnosis of T Cell-Related Pathology. *Am. J. Transplant.* 13, 2842-2854 (2013). These previous studies suggest a role for IR in transplant rejection, but do not provide critical diagnostic tools for identifying patients at risk of transplant rejection. Meanwhile, BCR-Seq has been applied to study diseases and human immune responses such as multiple sclerosis, influenza vaccine or immunodeficiency disorders (Palanichamy, A. et al. Immunoglobulin class-switched B cells form an active immune axis between CNS and periphery in multiple sclerosis. *Sci. Transl. Med.* 6, 248ra106-248ra106 (2014); Strauli, N. B. & Hernandez, R. D. Statistical inference of a convergent antibody repertoire response to influenza vaccine. *Genome Med.* 8, 60 (2016); and Roskin, K. M. et al. IgH sequences in common variable immune deficiency reveal altered B cell development and selection. *Sci. Transl. Med.* 7, 302ra135 (2015)), however there is a deficit of studies in transplant rejection. In Ktx, BCR-Seq has been utilized in the study of tolerance (Massart, A., Ghisdal, L., Abramowicz, M. & Abramowicz, D. Operational tolerance in kidney transplantation and associated biomarkers. *Clin. Exp. Immunol.* 189, 138-157 (2017). BCR-Seq has also been applied to study HLA-sensitized Ktx candidates undergoing desensitization therapy (Beausang, J. F. et al. B cell repertoires in HLA-sensitized kidney transplant candidates undergoing desensitization therapy. *J. Transl. Med.* 15, 9 (2017)). Lastly, BCR-Seq has been applied to study B-cell infiltration comparing clonal expansion in blood and graft (Ferdman, J. et al. Expansion and somatic hypermutation of B-cell clones in rejected human kidney grafts. *Transplantation* 98, 766-72 (2014)). Additionally, BCR-Seq was applied to measure the temporal response of the B cell repertoire to immunosuppression after heart transplantation sin a small cohort of 12 heart transplant recipients (Vollmers, C. et al. Monitoring Pharmacologically Induced Immunosuppression by Immune Repertoire Sequencing to Detect Acute Allograft Rejection in Heart Transplant Patients: A Proof-of-Concept Diagnostic Accuracy Study. *PLOS Med.* 12, e1001890 (2015).

While these prior art investigations have provided some insight into the role of the IR in transplant rejection, they have not yielded a diagnostic tool that can assess transplant risk in subjects prior to transplant or thereafter. Accordingly, there remains a need in the art for novel methodologies to assess transplant risk pre-transplant and to successfully monitor transplant recipients for rejection post-transplant.

SUMMARY OF THE INVENTION

The several inventions of the present disclosure include a method to identify a prospective graft recipient's predisposition to reject a donor organ. An immune risk assessment for rejection can be generated for each donor-recipient pair before performing a transplant procedure Additionally, the inventors of the present disclosure have identified critical dynamics in IR diversity that are predictive of transplant rejection after transplant. Also, the inventors of the present disclosure have discovered certain immune elements that can serve a biomarkers of rejection risk.

Specifically, in one aspect, a subject's risk of transplant rejection may be assessed by measurement of one or more aspects of IR diversity, wherein subjects having a greater IR diversity prior to transplant are more susceptible to transplant rejection. In another aspect, a subject's risk of transplant rejection may be assessed by measurement of one or more aspects of IR diversity, wherein changes in diversity are indicative of transplant risk. In another aspect, the presence or elevated abundance of particular immune elements is used as a diagnostic biomarker of transplant rejection risk. In another aspect, the scope of the invention comprises kits for performing the diagnostic methods of the invention. In another aspect the scope of the invention encompasses methods of treating transplant rejection in a subject, by assessing transplant risk and administering immunosuppressive therapy in accordance with assessed risk.

BRIEF DESCRIPTION OF THE DRAWINGS

FIGS. 1A, 1B, 1C, and 1D are violin plots showing the number of clones (richness) that define the repertoire across the three clinical outcomes (NP, PNR and PR). FIG. 1A depicts the number of clones, assessed by genomic DNA at time 0 (prior to transplant). FIG. 1B depicts number of clones, assessed by genomic DNA at six months following transplant. FIG. 1C depicts number of clones, assessed by genomic DNA at 24 months following transplant. FIG. 1D depicts the number of clones for the IgD isotype at six months following transplant. The p-values are obtained from the adjustment of a linear model considering the number of clones as a dependent variable and clinical outcome as an independent factor variable.

FIG. 2A is a boxplot of the Cluster Gini Index Vertex Gini Index for each clinical outcome at 24 months following transplant. FIG. 2B is a boxplot of the Cluster Gini Index for each clinical outcome at 24 months following transplant. The p-values are obtained from the adjustment of a linear model considering the Gini(V) and Gini(C) as a dependent variable and clinical outcome as an independent factor variable for each time point.

FIGS. 3A, 3B, and 3C. FIGS. 3A, 3B, and 3C are boxplots showing IGHV3-23 clonal abundance at different time points for NP vs. PR. FIG. 3A depicts IGHV-23 clonal abundance at time 0 (p-value=0.04). FIG. 3B depicts IGHV-23 clonal abundance at six months (p-vlaue=0.003). FIG. 3C depicts IGHV-23 clonal abundance at 24 months (p-value=0.02).

FIG. 4 is an overview of an exemplary conditional growth model to find the association between richness and entropy with the clinical outcome at the different time points.

DETAILED DESCRIPTION OF THE INVENTION

Figure 1D:
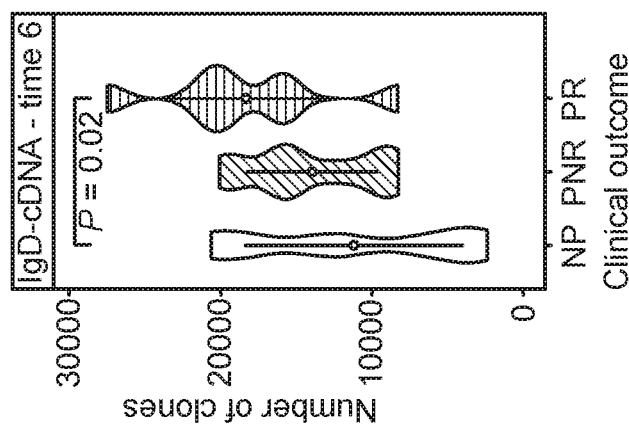
FIGS. 1A, 1B, 1C, and 1D.
Figure 1C:
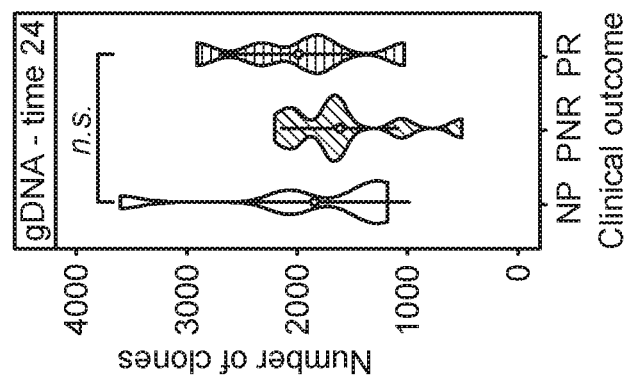
Figure 1B:
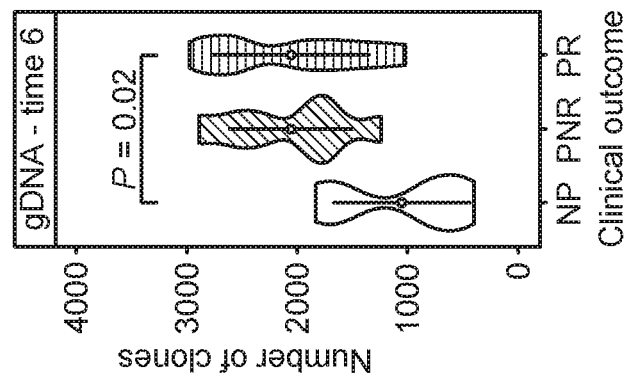
Figure 1A:
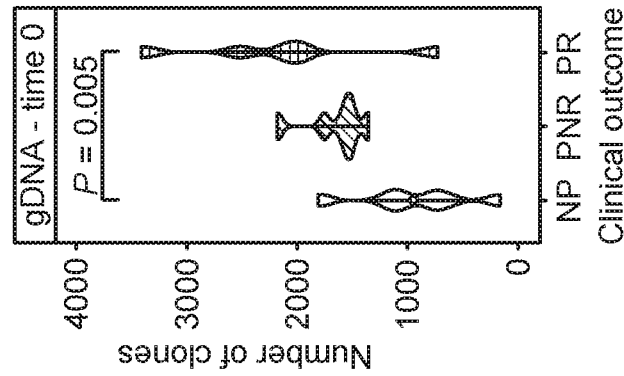

The several inventions disclosed herein are applicable in the area of assessing and treating transplant risk. The various elements of the invention are described next.

Immune Elements. The methods of the invention require assessing immune repertoire diversity in a subject. Immune repertoire diversity, as used herein, refers to the diversity of one or more selected immune elements in the subject. An "immune element," as used herein, comprises any type or subtype of immune receptor which is subject to diversification for selectively binding an antigen.

Immune element diversification occurs in the lymphoid compartments where immune cells are generated. Diversity is generated by what is known as V(D)J recombination, wherein random recombination of "V" (for variability) gene segments, "J" (for joining) gene segments, and for some elements, "D" (for diversity) gene segments takes place, resulting in millions of different variable region gene coding sequences. These, in turn, are translated to produce an immense number of variable region amino acid sequences. The majority of the diversity on an immune element is found on three areas of the variable region, known as the complementarity determining regions or CDRs: CDR1, CDR2, and CDR3. CDR3 is the most diverse of the three CDRs.

A first immune element class is the immunoglobulins. Immunoglobulins may be present as secreted antibodies or as B cell surface receptors. B cell genomic DNA, produced by the aforementioned V(D)J recombination, codes for variable regions of heavy and light chains. Immunoglobulins (Igs) are produced in several forms, including the IgA, IgD, IgE, IgG, and IgM isotypes.

Various sequencing methods, as described below, may be used to selectively amplify and measure the abundance of different types of Igs. Accordingly, in assessing IR diversity, any number of Ig types may be selected as the studied immune element for IR diversity characterization. In one embodiment, the immune element comprises all immunoglobulins. In one embodiment, the immune element comprises immunoglobulins of a selected isotype, including IgA, IgD, IgE, IgG, or IgM isotypes. In one embodiment, the immune element comprises the light chain variable region. In one embodiment, the immune element comprises a heavy chain variable region. In one embodiment, the immune element comprises an Ig CDR selected from CDR1, CDR2 and CDR3. In one embodiment, the immune element is a B cell receptor. In embodiment, the immune element is a secreted antibody Ig. It will be understood by one of skill in the art that an immune element may comprise two or more different Ig subtypes. For example, an Ig may be an IgG light chain CDR3 region comprising a B cell receptor. In another example, the Ig may be a heavy chain CDR2 variable region of a secreted IgM antibody, etc.

A second class of immune elements is the T cell receptors (TCRs), which are present on the surface of certain T cells. Like Igs, the TCRs are characterized by immense protein sequence diversity which is present in the variable regions of the TCR. TCRs are present as heterodimers of different cell receptors are produced by lymphatic cells, in this case, lymphatic cells of the thymus. The T cell receptor variable regions are present in heterodimers, mostly dimers of the alpha ($\alpha$) chain and a beta ($\beta$) chain. A fraction of TCRs comprise dimers of gamma and delta chains.

As with Igs, different types of TCR components may be selectively amplified and sequenced. Accordingly, different TCR components may be utilized as the selected immune element to characterize IR diversity. In one embodiment, the immune element is all TCRs. In one embodiment, the immune element comprises an alpha/beta TCR heterodimer. In one embodiment, the immune element comprises a gamma/delta heterodimer. In one embodiment, the immune element is a TCR chain type, selected from the group consisting of alpha, beta, gamma, and delta chains.

Immune Element Diversity. The methods of the invention utilize various measurements of immune element diversity. In such analyses, immune elements are defined as clonotypes or "clones," each clone being a specified immune element (e.g. a B cell receptor or T cell receptors) having a defined sequence, or belonging to a defined set of sequences by which related clones having similar sequences are grouped. Clonotype may be specified by any set of criteria known in the art, for example, known clonotype specifications such as: having the same CDR3 amino acid sequence; having sequences within a cluster of related CDR3 sequences; having the same variable chain region sequences (e.g. IGV light or heavy chain sequences).

For example, in one implementation, the clonotype is defined as as a group of cells having one or more characteristics selected from the group consisting of: descended from a common ancestor molecule; having the same IGHV segment; having the same IGHJ segment; having CDR3 sequences of the same length; and having 90% nucleotide identity between CDR3s.

Reference will be made herein to sequences, specifically, the sequences of selected immune elements. As used herein, sequence refers the amino acid sequence of a selected element, for example, the alpha chain of a TCR. Sequence will also refer to the nucleotide sequence of the gene (or transcript thereof) which codes for the specified polypeptide. Unless specified or clearly denoted by context, reference to a clone's sequence will be understood to encompass both the amino acid sequence of a specified element and the polynucleotide sequence(s) coding therefor.

Diversity, as known in the art, generally refers to the number of unique immune element species, and is generally thought to reflect the variability of antigenic specificities in the immune system of a subject. Immune elements are present in complex populations, i.e. T cell and B cells, with different subtypes of each, wherein a number of unique species are present, in unequal abundance (frequency). Accordingly, diversity may be quantified in various ways. For example, in one implementation, diversity is quantified as species richness, i.e. the absolute number of different immune elements of a selected type. In another implementation, diversity is expressed as a diversity index, for example Shannon entropy. In such measures, the diversity of the IR is based on weighted measures of clonal abundance, giving a measure of the effective number of unique immune elements. Diversity, in the practice of the invention, may be assessed by any method known in the art, for example by exponential Shannon-Weiner, inverse Simpson, or Berger-Parker indices.

For example, diversity may be measured by methods based on any of the methods described in: Miho et al., Computational strategies for dissecting the high-dimensional complexity of adaptive immune repertoires, 2018, Front Immunol 9: 224; Wardeman and Busse, Novel Approaches to Analyze Immunoglobulin Repertoires, 2017, Front Immunol 38:471-482; and Grieff et al., Bioinformatic and Statistical Analysis of Adaptive Immune Repertoires, 2015, Trends Immunol 36:738-749.

Measurement of IR Diversity. The selected measure of IR diversity may be achieved by methods known in the art for quantification of clones. Such measurements will be carried out using a sample derived from a subject.

In one implementation, immune repertoire diversity is assessed by nucleic acid sequencing of B cells or T cells. These cells may be extracted from any suitable substance or compartment of the subject. In a first embodiment, the sample may comprise a peripheral blood sample. Such samples are conveniently withdrawn in standard procedures. In the case of B cells, samples may alternatively be derived from bone marrow, lymph, or secondary lymphoid organs, such as the spleen or lymph nodes. In the case of T cells, samples may alternatively be derived from the bone marrow or thymus. Other sample types may include kidney biopsy material, urine or any biofluid representative of IR diversity. The sample may comprise DNA, RNA, proteins, or other materials that can be sequenced or otherwise assessed to determine immune receptor diversity.

The sample is derived from a subject. The subject may be a human. In alternative embodiments, the subject may be an animal such as veterinary patient or test animal. The subject may be a transplant recipient (i.e. an individual post-transplant that has received one or more grafts) or a putative transplant recipient, (i.e. a pre-transplant individual in need of a graft). The graft received or to be received may comprise any transplanted tissue, organ, or body part. Exemplary graft types include the kidney, heart, lung, liver, skin, cornea, intestine, pancreas, limb, digit, etc. In one embodiment, the graft is a kidney graft.

In one implementation, clonal populations are quantified by sequencing of genomic DNA of T cells, B cells, or both. This measure provides a count of total clonal diversity at the genetic level. In one implementation, clonal populations are quantified by sequencing of RNA produced CDNAs produced by T cells, B cells, or both. This measure provides an accounting of clonal diversity at the transcriptome or expression level and captures the frequency of each clone's abundance.

Sequencing of the selected nucleic acids may be achieved by any suitable method known in the art. Exemplary methodologies include any high-throughput massively DNA sequencing techniques. Exemplary sequencing technologies include 454™ sequencing, Illumina™ sequencing, and ion torrent methods. Various primer sets known in the art for the sequencing of immune receptor sequences may be used. The methods of the invention may employ any estimator of species richness known in the art, for example, DNA barcoding, exhaustive sequencing, 5' RACE or other unbiased sequencing techniques, spectratyping, non-parametric abundance estimators, parametric estimators, the Chao1 estimator, Chao1-bc estimator, Chao2 estimator, abundance-based coverage estimator, incidence-based coverage estimators, f Poisson abundance models, and rarefaction curves.

Exemplary methods include those described in PCT International Patent Application Publication Number 2014144713, entitled Methods of Sequencing the Immune repertoire, by Hutchins and Fan; PCT International Patent Application Publication Number 2014043813, entitled Immune repertoire profiling, by Holt; and U.S. Pat. No. 9,279,159, entitled Quantification of adaptive immune cell genomes in a complex mixture of cells, by Robins et al.

In one embodiment, the selected clonotype is B cell receptors and the selected method of measuring B cell receptor diversity is a BCR-Seq methodology, as known in the art. For example, in one implementation, the BCR-Seq method encompasses the use of barcoded libraries, for example, multiplexed primers to the IgH J or FR1 or FR2 framework regions per the BIOMED-2 design, as described in van Dongen, J. J. M. et al. Design and standardization of PCR primers and protocols for detection of clonal immunoglobulin and T-cell receptor gene recombinations in suspect lymphoproliferations: Report of the BIOMED-2 Concerted Action BMH4-CT98-3936. *Leukemia* 17, 2257-2317 (2003).

In one embodiment, paired-end reads are merged using FLASH (Mag, T. & Salzberg, S. L. FLASH: fast length adjustment of short reads to improve genome assemblies. 27, 2957-296310 (2011)), wherein, after sequences are demultiplexed and trimmed of barcodes and primer sequences, the V, D, and J regions and V-D (N1), D-J (N2) junctions are identified using the alignment program IgBLAST (Ye, J., Ma, N., Madden, T. L. & Ostell, J. M. IgBLAST: an immunoglobulin variable domain sequence analysis tool. *Nucleic Acids Res.* 41, W34-40 (2013)). Sequences may be filtered to remove non-clonotype artifacts, sequences with V-gene insertion or deletions, chimeric sequences and non-functional sequences.

The scope of the invention includes the use of the aforementioned sequencing techniques and further encompasses any other methodology for assessing or estimating IR diversity. For example, antibody profiling techniques, such as antigen arrays, may be used to assess IR funcational diversity. Diversity may be measured by species richness considering the number of clones per sample and Shannon entropy (H) to measure diversity providing information about the size-distribution of species in the population for example, wherein H is defined as:

$$H = -\sum_{i=1}^{N} p_i \log_2 p_i$$

where N is the number of unique clones and $p_i$ is the frequency of clone i. H ranges from 0 (sample with only one clone) to Hmax=$\log_2$N (sample with a uniform distribution of clones).

Transplant Rejection. The scope of the invention encompasses various methods of assessing transplant rejection risk and methods of treating and preventing transplant rejection. Transplant rejection, as used herein, encompasses any form of graft injury mediated by the immune system, including accute or chronic forms of graft rejection. Exemplary manifestations of rejection include chronic allograft maculopathy, T-cell mediated responses against foreign MHCs in the donated organ, Type III or Type IV hypersensitivity, leukocyte infiltration of the graft vessel, intimal thickening and fibrosis of graft vessels, organ atrophy, and organ dysfunction. Outcome can be assessed by any measure of transplant injury, for example, graft function, DSA, proteinuria levels, panel reactive antibody (PRA) assessment, or histology-based measures of graft injury (e.g., iFTA, cg, C4d, Banff grade, etc.).

For example, in one implementation, rejection status is classified by clinical phenotype groups, for example, based on defined pathology reads of allograft biopsies, for example, as scored by Banff criteria. In another implementation, rejection status is based on a chronic allograft damage index (CADI) score, as known in the art. In one implementation, subjects may be classified as: non-progressors (NP) with low non-incremental CADI score without acute rejection over a selected time period; progressors with no rejection (PNR), having incremental CADI score without rejection over the selected time period; and progressors with rejection (PR) having high incremental CADI scores with one or more rejection episodes over the selected time period.

Determination of Transplant Rejection Risk in Prospective Recipients. In a first aspect, the invention is based on the discovery that pre-transplant IR diversity is indicative of post-transplant rejection risk. Such methods enable the assessment of a subject's suitability for receiving a transplant. The inventors of the prsent disclosure have determined that, generally, subjects with a relatively higher diversity of immune elements prior to transplant are more likely to experience adverse rejection events following transplant. Accordingly, in one implementation, the invention encompasses a method of assessing transplant rejection risk in a subject as follows:

obtaining a sample from the subject;
assessing a measure of the subject's immune repertoire diversity by the sample;
comparing the measured immune repertoire diversity to a predetermined threshold to determine the subject's risk of transplant rejection, wherein, if the subject's measured immune repertoire diversity is above the threshold; the subject is considered to have an increased risk of transplant rejection, and/or if the subject's measured immune repertoire diversity is below the threshold value, the subject is considered to have a reduced risk of transplant rejection.

The method of the invention utilizes a statistically validated threshold value. The statistically validated threshold value is a value or range of values of a selected IR diversity measurement that can be used to distinguish subjects at elevated risk of transplant rejection from those of lower risk of transplant rejection.

Such threshold or cut-off may be selected by methods generally known in the art to provide for a chosen sensitivity and/or specificity of the risk assessment, e.g., sensitivity and/or specificity of at least 50%, or at least 60%, or at least 70%, or at least 80%, or at least 85%, or at least 90%, or at least 95%. The designation of "elevated risk" may be selected at any chosen level of risk, for example, a probability of rejection, for example, an elevated probability of rejection greater than 5%, greater than 10%, greater than 20%, greater than 30%, greater than 40%, greater than 50%, greater than 60%, greater than 70%, greater than 80%, or greater than 90% probability. In one implementation, the diversity measure comprises a probability score, i.e. a measure of the likelihood that the subject will experience one or more selected rejection events.

The threshold values of the invention may be established using any statistical methods known in the art and suitable for associating IR diversity to transplant outcome. For example, thresholds may be established by a use of a historical prospective study, a retrospective cohort study, or like study of relevant subjects wherein the selected measure of IR diversity is quantified in a pool of appropriately matched subjects (e.g. subjects receiving the same graft type as the subject, subjects having similar health and demographic factors, etc.) using like measures of diversity and wherein one pool of subjects experienced rejection and one pool of subjects did not experience rejection over a selected time period following transplant. Exemplary methods of generating thresholds include logistic regression, linear regression methods, machine learning classifiers such as random forest, support vector machines, and deep learning and neural network approaches.

The data may be used to generate a classifier, as known in the art, for example, a classifier indicating that the subject is at risk or not. The output of the classifier may be a probability or categorical risk score, for example, "low risk," "intermediate risk," and "high risk."

For example, in one embodiment, the determination of threshold values is accomplished by a general linear model to find the association between the selected measure of IR diversity and clinical outcome at selected time points, for example, a linear-mixed effect model.

The predictive method of the invention may advantageously be used to screen potential graft recipients for transplant rejection risk. In one implementation, this method is used to optimize transplant allocations, for example, where the availability of the selected graft is limited and it is desired to match the graft to the most compatible subjects.

In one embodiment, the graft type comprises a kidney graft. In one embodiment, the selected unit of IR diversity is BCR diversity. In one embodiment, the selected measure of IR diversity is species richness. In one embodiment, the selected measure of IR diversity is a diversity index, for example, a Shannon entropy index. In one embodiment, the thresholds are selected to distinguish likely non-progressors from progressors without rejection and/or progressors with rejection.

Monitoring Transplant Rejection Risk Post-Transplant. In another aspect, the scope of the invention is directed to monitoring transplant rejection risk in subjects that have previously received a transplant. The inventors of the present disclosure have advantageously determined that changes in IR diversity following transplant are correlated with transplant outcome. Specifically, subjects at risk of transplant rejection were found to experience a reduction in IR diversity over time following transplant, whereas subjects at lower risk of transplant rejection were found to have an increase in IR diversity following transplant.

Accordingly, the scope of the invention encompasses a method of assessing transplant rejection risk in a subject, comprising the steps of:
  obtaining a sample from the subject at a first time point and a second time point;
  for each of the first and second time points, assessing a measure of the subject's immune repertoire diversity by the sample;
  comparing the measured diversity at the first and second time points, wherein a decrease in IR diversity between the two time points is associated with an elevated risk of transplant rejection and/or an increase, in IR diversity between the two time points is associated with a reduced risk of transplant rejection.

In one embodiment, the two time points are (1) a time point prior to receipt of transplant by the subject and (2) two time points after receipt of the graft (for example, at 6 months and 24 months). In one embodiment, both time points are after receipt of a transplant by the subject.

An "increase" or "decrease" in IR diversity may be determined by any statistically relevant measure, for example, a change in absolute diversity value or a relative change in diversity value that exceeds a specified threshold. In some implementations, increase or decrease is assessed with respect to more than two time points to identify trends over time. The establishment of statistically relevant "increase" or "decrease" may be achieved by any appropriate statistical methodology for associating changes in IR diversity over time with transplant outcome, for example, using appropriately matched pools of subjects that experienced a selected rejection event and those that did not, over a selected time period following transplant receipt.

Figure 4:
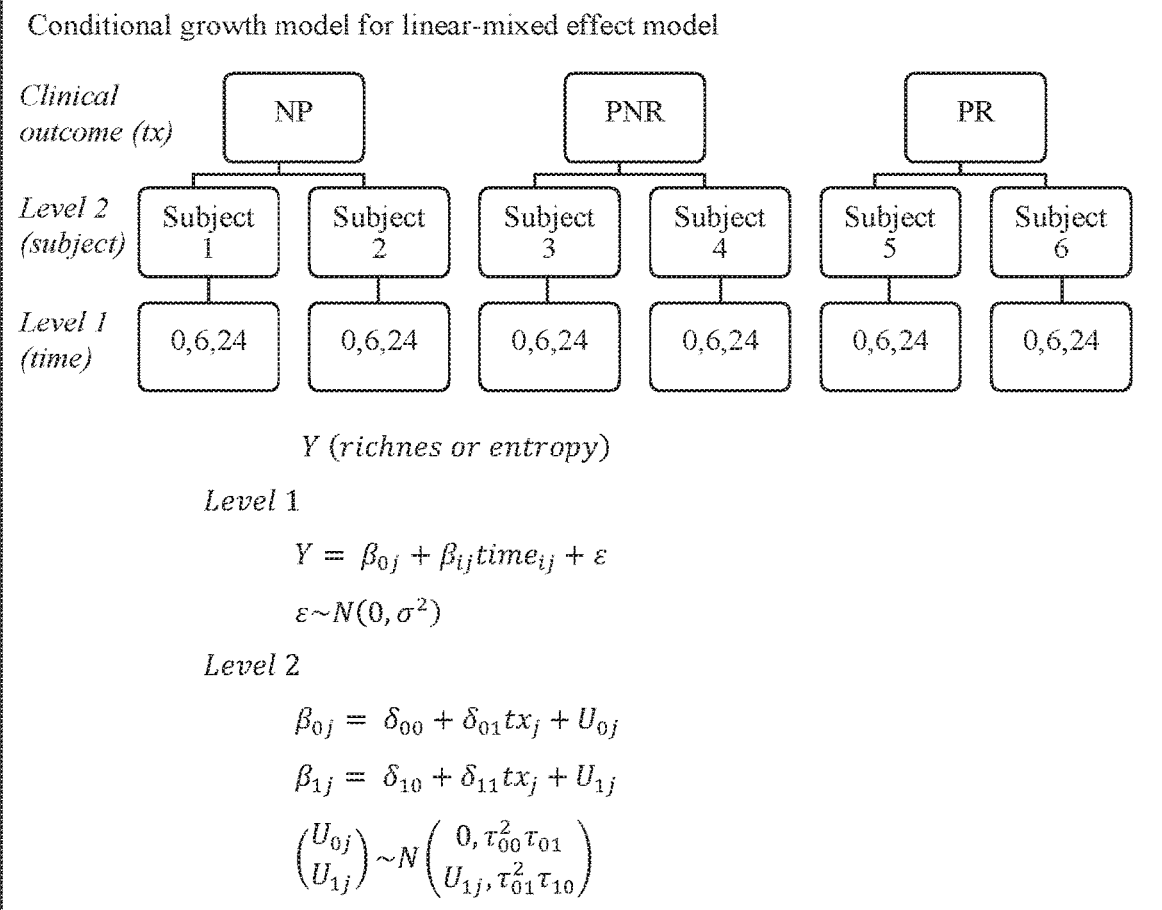
FIG. 4.

For example, in one embodiment, a linear-mixed effect model considering a conditional growth model may be applied to rejection outcome and IR diversity data, as depicted in FIG. 4

The method of the invention allows for monitoring of transplant rejection risk in graft recipients following graft receipt. For example, in one implementation, the subject is the recipient of a kidney graft. In one embodiment, the selected measure of IR diversity is B cell receptor diversity. In one embodiment, the B cell receptor diversity is assessed by BCR-Seq methods. In one embodiment, the selected rejection event is progression with rejection, for example, as established by CADI score.

Clonal Biomarkers of Rejection Risk. The inventors of the present disclosure have determined that certain clones are highly represented in subjects at risk of rejection. Specifically, the presence of immune elements comprising IGHV3-23 (immunoglobulin heavy chain V-gene 3-23) segments is indicative of transplant rejection risk. In one embodiment, the scope of the invention encompasses a method of assessing transplant risk in a subject, comprising
  obtaining a sample from the subject;
  assessing the abundance of selected clonotypes comprising IGHV3-23 sequences in the sample;
  comparing the abundance of selected clonotypes comprising IGHV3-23 sequences to a predetermined threshold to determine the subject's risk of transplant rejection, wherein, if the subject's measured abundance of the clonotypes comprising IGHV3-23 sequences is above the threshold, the subject is considered to have an increased risk of transplant rejection and if the subject's measured abundance of the selected clonotypes comprising IGHV3-23 sequences is below the threshold value, the subject is considered to have a reduced risk of transplant rejection.

A clonotype comprising IGHV3-23 sequence is any clonotype comprising sequences (i.e. amino acid sequences or nucleic acid sequences coding therefor) which are uniquely specified by the IGHV23 gene. In one embodiment, the IGHV3-23 gene is a human IGHV3-23 gene, as known in the art, for example as specified by NCBI taxonomy database Gene ID number 28442, Protein ID number 9606. In one embodiment the clonotype IGHV3-23 sequences comprises 3, 4, 5, 6, 7, 8, 9, 10, or more nucleotides of the IGHV3-23 gene sequence. In one embodiment, the IGHV3-23 sequence comprises 3, 4, 5, 6, 7, 8, 9, 10, or more amino acids of the IGHV3-23 protein sequence. The sequences may be contiguous or may include one or more intervening variable nucleic acids or amino acids.

In one embodiment, the clonotype is defined by a B cell genomic DNA sequence. In one embodiment, the clonotype is defined by a B cell transcript abundance. In one embodiment, the clonotype is a B cell receptor. In one embodiment, the clonotype is a secreted immunoglobulin. In one embodiment, the clonotype is a T cell receptor.

In one embodiment, the subject is a human subject. In one embodiment, the subject is a prospective transplant recipient and the risk of rejection is assessed prior to transplant. In one embodiment, the subject is a subject that has received a transplant and the risk of rejection is an assessment of ongoing risk.

In one embodiment, the threshold value is a statistically determined cutoff above which risk of rejection is elevated by, for example, 5% or more, 10°/© or more, 15% or more, 20% or more, 25% or more, 30% or more, 35% or more, 40% or more, 45% or more, 50% or more, 55% or more, 60% or more, 70% or more; 80% or more, or 90% or more than in subject not meeting the threshold value.

Differentiating Between Types of Rejection. In one embodiment, the methods of the invention are utilized not only to determine the risk of transplant rejection and graft injury, but also to differentiate between the types of transplant rejection risk. For example, in one implementation, an elevated risk of transplant rejection is determined by the methods of the invention, for example, by elevated IR diversity prior to transplant, by increasing IR diversity following transplant, or by elevated abundance of IGHV3-23 immune elements, wherein the type of immune element is indicative of the type of transplant rejection risk. For example, in one embodiment, one or more measures of T cell receptor diversity is applied, and if an elevated risk of transplant rejection is detected by such assessment, the subject is deemed to have an elevated risk of T-cell mediated rejection. Likewise, in another embodiment, one or more measures of B receptor or immunoglobulin diversity is applied, and if an elevated risk of transplant rejection is detected by such assessment, the subject is deemed to have an elevated risk of antibody-mediated rejection. In one embodiment, one or more measures of T cell receptor diversity is applied and, one or more measures of B receptor or immunoglobulin diversity is applied, such that risk for both types of rejection may be detected.

Methods of Treatment The scope of the invention further encompasses methods of treatment that employ the predictive methods described above. In a first aspect, the scope of the invention includes a method of providing a graft to a subject in need thereof, comprising the following steps:

assessing the risk of transplant rejection in the subject by
  obtaining a sample, assessing a selected measure of IR diversity, and comparing the assessed measure of IR diversity against a threshold value, wherein, if the subject's measured IR diversity is below the threshold value, the subject is deemed to be at a reduced risk of transplant rejection; and
performing a graft transplant on the subject, if the subject is determined not to have an elevated risk of transplant rejection and/or if the subject is determined to a reduced risk of transplant rejection.

By this method, transplants are provided to subjects not having an elevated risk of transplant rejection and/or having reduced risk of rejection, leading to improved clinical outcomes. In one embodiment, the subject is a subject in need of a kidney graft. In one embodiment, the selected measure of IR diversity is BCR diversity. In one embodiment, BCR diversity is assessed by BCR-Seq. In one embodiment, the threshold value is determined by comparison of clinical outcomes in pools of subjects stratified by CADI scores.

In another aspect, the scope of the invention encompasses methods of treating immune rejection risk in a subject comprising a prospective graft recipient or a graft recipient and having an elevated risk of transplant rejection. In one embodiment, the method of treating transplant rejection risk comprises administering an immunosuppressive treatment to the subject. For example, the method may comprise the steps of assessing the risk of transplant rejection in the subject; and
administering an appropriate immunosuppressive treatment to the subject based on the assessed risk of transplant rejection.

In one implementation, the risk of transplant rejection is assessed prior to graft receipt and the treatment is a prophylactic treatment. In one implementation, the risk of transplant rejection is assessed after graft receipt. In one implementation, if the subject is determined have an increased risk of transplant rejection, an appropriate preventative immunosuppressive treatment is administered. In one embodiment, the appropriate immunosuppressive treatment is a more aggressive immunosuppressive treatment than the subject was receiving previously. In one implementation, if the subject is determined to be at a decreased risk of transplant rejection, the appropriate immunosuppressive treatment is a less aggressive immunosuppression than was administered to the subject previously.

The immunosuppressive treatment may be any treatment known in the art, for example, treatments appropriate a for high risk transplant patient or preventative treatment applied to a subject at risk for acute graft injury. Exemplary treatments include increased frequency of monitoring for graft injury, more aggressive immune suppression, or other appropriate treatments for subjects at risk of immune graft injury. For example, immunosuppressive treatments may comprise the administration of glucocorticoids, calcineurin inhibitors such as cyclosporine and tacrolimus, antimetabolite agents such as azathioprine and mycophenolate mofetil, rapamycin inhibitors, such as sirolimus and everolimus, polyclonal antilymphocyte antibodies.

In one embodiment, the type of treatment is dictated by the type of rejection risk detected. For example, if T-Cell mediated risk is detected, the subject may be treated with additional immunosuppression with steroid treatments, as known in the art. If antibody mediated rejection risk is detected, this type of rejection is difficult to reverse and the subject may be prepared for a replacement transplant procedure, for example, by securing access to an additional graft, increased frequency of monitoring for rejection, and other steps routinely performed for subjects at elevated risk of antibody mediated transplant risk.

Kits and Software. The scope of the invention further encompasses kits for performing the predictive methods of the invention. For example, the kits of the invention may comprise collections of reagents specially suited for performing a selected diversity analysis. For example, in one embodiment, the kit comprises a library preparation kit optimized for the detection of the selected immune element sequences. For example, in one embodiment, the kit comprises a library preparation kit for the detection of BCR sequences. In one embodiment, the kit comprises a collection of PCR primers for the selective amplification of the target immune elements. In one embodiment, the kit comprises a collection of oligonucleotide barcodes for the selective amplification and identification of the selected immune elements. In one embodiment, the kit comprises a collection of compositions of matter for the detection of immune elements comprising IGHV3-23 sequences.

In one embodiment, the scope of the invention encompasses a computer readable medium tangibly storing computer-readable instructions which carry out one or more operations of the invention on a general purpose computer. For example, the tangible medium may enable a general purpose computer to perform sequence identification, alignments, and other steps to quantify selected clonotypes from sequencing data, to calculate values of IR diversity, and to compare calculated values of IR diversity to statistically validated threshold values, or to output the results of the analysis to a display device. For example, in one embodiment, the tangible medium may comprise a program for classifying sequence reads, quantifying clonotypes, and determining transplant risk thresholds for kidney transplant recipients by means of a BCR diversity analysis.

EXAMPLES

Example 1. Immune Repertoire Diversity and Transplant Outcome in Kidney Transplant Recipients Study Subjects: 81 samples for gDNA and 56 matched samples for cDNA were studied longitudinally at time 0, 6 and 24 months from a total number of 27 recipients who went through a kidney organ transplant. All patients received an immunosuppressive regimen consisting of a combination of tacrolimus, mycophenolate mofetil and daclizumab or thymoglobulin induction. Some patients received a steroid-avoidance regimen, while others received a steroid-based immunosuppressive regimen.

All the samples used in the study had an associated serial allograft biopsy which was read by a central pathologist, using semi-quantitative histological scores for both acute rejection by the modified Banff criteria and for chronic allograft injury, using the chronic allograft damage index (CADI) score. The patients were classified in three clinical outcomes defined by CADI score and rejection episodes Non-progressors (NP) had low non-incremental CADI score on 3 serial biopsies over 2 years, without acute rejection, progressors with no rejection (PNR) had higher CADI score on their serial biopsies over 2 years and incremental across the time points without rejection, and progressors with rejection (PR) had incremental high CADI scores on their serial biopsies over 2 years with rejection episodes. These patients were matched for demographic variables, and for all NP, and PNR to have no evidence inflammation on biopsy, or sub-clinical injury as measured by absent donor specific antibodies.

Isolation of gDNA and RNA: Blood samples (4.5 mL) were collected and incubated at room temperature for 30 min until a clot was formed. The sample was then centrifuged and the upper layer of serum was then transferred to another cryotube and the clot was stored in the same tube at −80° C. until use. Genomic DNA from whole blood clot was extracted by commercially available kits. For RNA extraction from kidney needle biopsy; total RNA was extracted and RNA quantity and integrity were determined with commercially available kits.

B-Cell Sequencing: Genomic DNA templated PCR reactions were prepared from 100 ng gDNA aliquots to generate 6 independent barcoded libraries per sample. Multiplexed primers to the IgH J or FR1 or FR2 framework regions per the BIOMED-2 design were used. 10-nucleotide barcode sequences' in the primers were used to indicate the sample identity and replicate library identity for each PCR reaction. PCR was performed with and a second PCR reaction was carried out next to ensure that libraries were not amplified to saturation prior to gel purification and sequencing. 0.4 µl of each first PCR product templated the second PCR reaction using external primers specific for the 454 linker sequences; the amplification was carried out by standard procedures. cDNA was synthesized from total 300 ng of RNA with priming by random hexamers. Templates were amplified by PCR using IGHV primers in framework 1 (FR1) and isotype specific primers located in the first exon of the constant regions. These primers also encoded approximately half of the Illumina linker sequences needed for cluster generation and sequencing. Sample identity was encoded by 8-nucleotide multiplex identifier barcodes in each primer. For Illumina cluster recognition, 4 randomized nucleotides were encoded in the primers immediately after the Illumina linker sequence in the constant region primers. Each antibody isotype for each sample was amplified in a separate PCR reaction, to prevent formation of cross-isotype chimeric PCR products. A first PCR was carried out, followed by a second PCR step to add the remaining portion of the Illumina linkers to the amplicons, using 0.4 microliters of the first PCR product as template in a 30 microliter reaction. The products of each PCR reaction were pooled in estimated equimolar amounts, electrophoresed on agarose gels, and gel extracted. High-throughput sequencing of genomic DNA templated libraries was performed on the 454™ (Roche). cDNA library sequencing was performed using 600-cycle sequencing kits.

Sequencing reads were processed as previously described in Looney, et al. Human B-cell isotype switching origins of IgE. *J. Allergy Clin. Immunol.* 137, 579-586.e7 (2016) and Roskin et al. IgH sequences in common variable immune deficiency reveal altered B cell development and selection. *Sci. Transl. Med.* 7, (2015). Paired-end reads were merged using FLASH where after sequences were demultiplexed and trimmed of barcodes and IGHV primer sequences. The V, D, and J regions and V-D (N1), D-J (N2) junctions were identified using the alignment program IgBLAST. Sequences were filtered to remove non-IGH artifacts, sequences with V-gene insertion or deletions, chimeric sequences and non-functional sequences. At sample level, those with less than 100 clones were excluded (defined by same V and J segments, same CDR3 length and 90% nucleotide identity) as a control for bad quality samples. After quality control, for gDNA complete longitudinally data was available for 69 samples at time 0, 6 and 24 with a total number of 327,703 reads (mean 4,045 per sample). For cDN, complete data was available for 55 matched samples, although no time 0 samples were further available, with isotype-specific information (1,773,330 reads for IgD (31,667 per sample), 1,708,227 reads for IgM (30,504 per sample), 973,444 reads for IgA (17,383 per sample), 139,7345 reads for IgG (24,953 per sample), and 29,000 reads for IgE (5,178 per sample).

Diversity Analysis: Diversity was measured by species richness considering the number of clones per sample. This measure does not take into account the frequency of each species so also used Shannon entropy (H) was also used to measure diversity providing information about the size-distribution of species in the population, wherein. H is defined as:

$$H = -\sum_{i=1}^{N} p_i \log_2 p_i$$

where N is the number of unique clones and $p_i$ is the frequency of clone i. H ranges from 0 (sample with only one clone) to Hmax=$\log_2 N$ (sample with a uniform distribution of clones).

Next, a general linear model was used to find the association between richness and entropy with the clinical outcome at the different time points. The model was adjusted by all the clinical variables available showed in Table 1 to be sure that any of the characteristics of the patient was a confounding factor.

To model the longitudinal component of the data, linear-mixed effect model was applied, as in FIG. 4. The interaction between clinical outcome and time to find association with richness and diversity with time being a random effect was assessed as: lmer(y~time+tx+time*tx+(time|subject), data=data)

To deal with the missing-species problem (only a fraction of billions of cells in a repertoire are represented) and sequencing and/or experimental errors, performed two strategies were employed. First, a Recon (reconstruction of estimated clones from observed numbers) tool was used to deal with the missing-species problem. Recon is a modified maximum-likelihood method that outputs the overall diversity of a repertoire from measurements on a sample. Recon output accurate and robust estimates of a set of diversity measure, including richness and entropy allowing robust comparisons of diversity between individuals. Second, a down-sampling strategy was performed taking a random subset of reads for each sample equal to the smallest sequencing size, followed to the re-calculation of the B-cell clones to adjust by sequencing depth and deal with possible experimental errors. For gDNA, there samples with very low reads (<1000), and to avoid losing many sequences and a total of 9 samples were excluded that had less than 1000 reads. In the case of cDNA, this was not necessary. Ten random subsamples were generated to account for possible stochastic effects and diversity analysis was performed at each time point and the longitudinal data analysis on the mean value of ten independently down-samples diversity estimates.

Network Analysis: each vertex represented a B-cell sequence where the size is defined by all the identical sequences. Edges are calculated using the clone definition (same V and J segments, same CDR3 length and 90% nucleotide identity between CDR3s) and clusters represents each clone in the repertoire. The analysis was done using igraph package in R using the "layout with graphopt" option to generate the plot. To quantify the network, the Gini Index was calculated for vertex size and cluster size. Gini Index is a measure of unevenness extensively used to measure wealth distribution. It measures the inequality among values of frequency distribution. We used the Gini function from ineq package in R to calculate the Gini coefficient for vertex size and cluster size distribution. A Gini coefficient of zero expresses perfect equality and a Gini coefficient of 1 expressed maximal inequality.

Results. Three clinical phenotype groups, defined by blinded central pathology reads of serial allograft biopsies scored by Banff criteria and the chronic allograft damage index (CADI) score were considered in this study: Non-progressors (NP; n=10) had low non-incremental CADI score without acute rejection, progressors with no rejection (PNR; n=10) had incremental CADI score over 2 years without rejection, and progressors with rejection (PR; n=7) had incremental high CADI scores over 2 years with rejection episodes.

B-Cell Immune Repertoire Sequencing Output. BCR-Seq was done on genomic DNA (gDNA) samples extracted from blood clots on 81 samples from 27 Ktx recipients at 3 time-points (0, 6, 24 months). Sequencing obtained a total number of 327,703 reads (mean 4,045/sample) after quality control. For validation of the results and further evaluation of each isotype, RNA was additionally extracted from matched PBMC that were available for 55 samples, collected at the same time as the blood clot, and performed cDNA sequencing at greater depth obtaining 1,773,330 reads for IgD (mean 31,667/sample), 1,708,227 reads for IgM (mean 30,504/sample), 973,444 reads for IgA (mean 17,383/sample), 139,7345 reads for IgG (mean 24,953/sample), and 29,000 reads for IgE (mean 5,178/sample). Libraries for each isotype were amplified separately and then pooled for sequencing; therefore comparative numbers may not mean anything here.

A "clone" was defined as a group of cells descended from a common ancestor molecule, that have the same IGHV and IGHJ segment, same CDR3 length and 90% nucleotide identity between CDR3s as previously defined in studies of adaptive B-cell responses. This definition enables a study of diversity, overlapping or common clones, and/or clonal expansion in the context of alloimmunity in Ktx. For stringency of data analysis, samples with less than 100 clones were discounted (69 samples from gDNA and 55 samples from cDNA were left for further study. IgE isotype was discarded completely due to a very small number of reads). In addition, a patient in the NP group was excluded from subsequent analysis that had developed EBV+ post-transplant lymphoproliferative disease at 2.2 years post Ktx, characterized by proliferation of Epstein-Barr virus-infected B-cells.

Pre-Transplant B-Cell Diversity is Associated with Risk of Rejection. B-cell IR diversity was measured considering species richness (number of unique clones) and Shannon entropy across time points and clinical outcomes. The repertoire before Ktx in PR was significantly more diverse than in the NP (richness: p-value=0.005, entropy: p-value=0.01) with the same trend persisting at 6 months after Ktx (richness: p-value=0.02, entropy: p-value=0.02), and with no distinguishable group differences at 2 years post-Ktx. cDNA sequencing data post-Ktx showed the same trend in greater repertoire diversity at 6 months after transplant, predominantly for the IgD isotypes (richness: p-value=0.02, entropy: p-value=0.03. Representative results are depicted in FIG. 1A, FIG. 1B, FIG. 1C, and FIG. 1D. There was no confounding effect on the data from various demographic and clinical variables, such as recipient age, gender, race, donor source, type of immunosuppression, HLA mismatch and cause of renal failure. In another measure of IR diversity, SHM was evaluated, defined as the frequency of mutations in each V gene segment, and a trend was observed for higher number of SHM for PR before Ktx, and trend for higher SHM in the IgD isotype in PR at 6 months post Ktx (p-value=0.06).

The Immune Repertoire Diversity Changes Across Time by Clinical Outcome. To find whether the IR diversity changes across time by the clinical outcome, the longitudinal data was modeled using linear mixed effect models considering the interaction between clinical outcome and time. NP and PR behaved differently across time after Ktx showing an increase in diversity in NP and a decrease in diversity for PR, while for PNR the diversity remained invariable across time. This was observed for gDNA (richness: p-value=0.007, entropy: p-value=0.001) and all isotypes for cDNA, with the most significant differences in entropy being for IgM and IgD isotypes (IgA: p-value=0.07, IgD: p-value=0.02, IgG: p-value=0.05, IgM: p-value=0.04).

Network Analysis of B-Cell Repertoires Shows Significant Differences in Clonal Expansion and Clonal Dominance Between Clinical Outcome Groups. The B-cell repertoire can be naturally represented as a network based on sequence diversity. To quantify the network, the Gini index, which is an unevenness measure was applied to the vertex and cluster distributions. When applied to vertex size, Gini (V), the overall clonal nature is represented. If Gini(V) is closer to 1, vertices are unequal showing expansion of some of them, and closer to 0 otherwise. When applied to cluster size, Gini(C), clonal dominance is represented. If closer to 1, clusters are unequal and therefore represent dominant clones, if closer to 0, all clusters are of equal size.

Figure 2A:
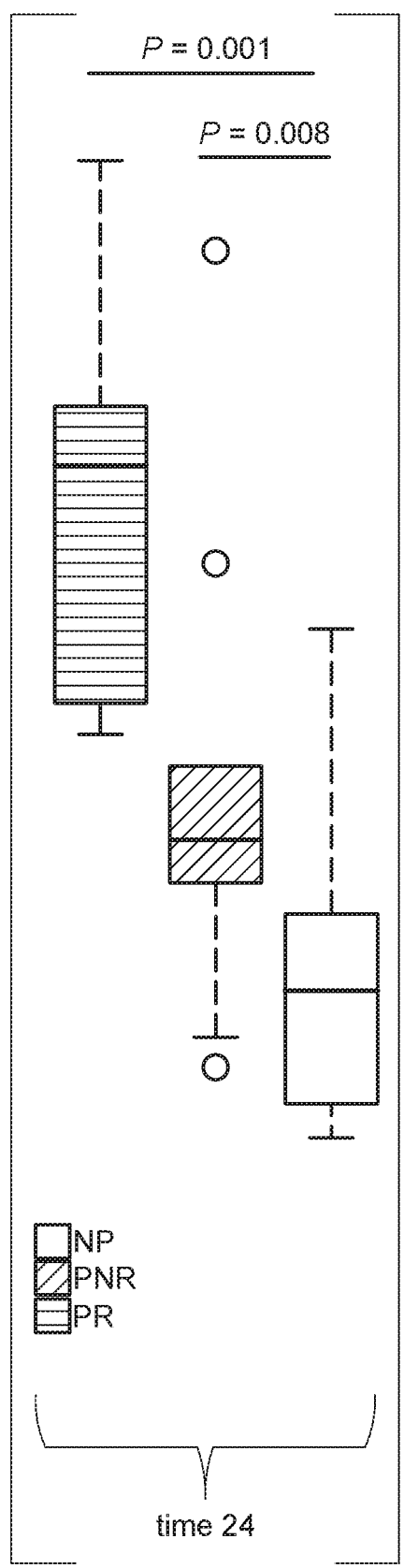
FIGS. 2A and 2B. Vertex Gini Index plotted against Cluster Gini Index for all the individuals in NP, PNR and PR differentiated by time points.
Figure 2B:
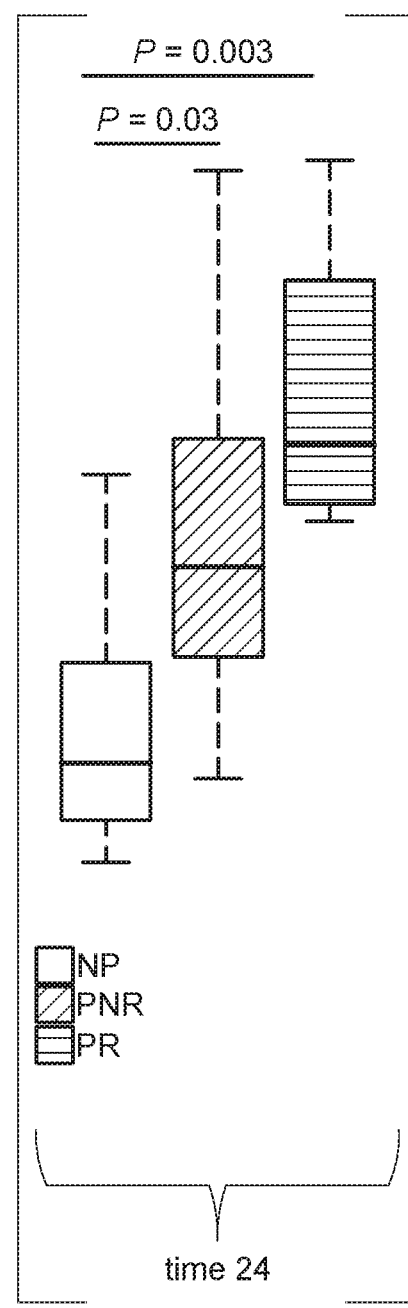

Marked visual and quantitative differences were observed between representative B-cell repertoires from each of the three clinical outcome groups, across the 3 different time points (pre-transplant, and post-transplant 6 and 24 months). In the PR repertoire, there was an abundance of B-cell sequences of a bigger size and larger clusters of clones in comparison with NP while PNR is located in between. Across time, the PR group shows a decrease in the number of BCR and unique clones in comparison with NP. On further evaluation of the Gini Index measure, the PR group consistently showed significantly higher measures for both the vertex and the cluster over the NP group, suggesting that the PR group patients had higher clonal expansion at baseline, and further post-transplant expansion of a sub-set of dominant clones (p-values<0.05). The PNR group locates between NP and PR as previously shown. Representative results are depicted in FIGS. 2A and 2B. The data generated for IgM isotype for cDNA showed the same trends as that from the gDNA data.

The results for cDNA sequences largely mirrored the results for genomic DNA.

IGHV3-23 Clones. For clonal analysis, the association of the presence or absence of each particular clone (118,223 total clones) with the clinical outcome (PR, PNR, NR) was assessed at each time point. IGHV3-23 gene usage per sample, defined as the number of times each IGHV3-23 gene has been used, normalized by the number of clones (to avoid sampling bias), filtering out low expressed genes (IGHV3-23 gene usage>0.05 in at least 10% of the samples), and applying a linear model to find those genes that were associated with each clinical outcome, at each time point. IGHV3-23 was the most significant and abundant gene across all 3 time points (NP vs. PR (time 0: p-value=0.04, time 6: p-value=0.003, time 24: p-value=0.02) (FIGS. 3A, 3B, and 3C). There was no confounding effect on the data from various demographic and clinical variables, such as recipient age, gender, race, donor source, type of immunosuppression, HLA mismatch and cause of renal failure. In addition, this gene was also found to be significant in both the IgM (p=0.008) and IgD (p=0.05) isotypes at 24 months post-Ktx, in concordance with the previous results showing consistency with these two isotypes being most enriched in the PR group.

Discussion. In this study, we it was observed that stable individuals had a reduced diversity of the B-cell IR before Ktx in comparison with those who rejected the organ. Further, the IR behaves differently across time depending on the clinical outcome group. For subjects having post-Ktx rejection of the organ, the B-cell diversity is initially higher and then decreased over time, whereas the reverse diversity trend was seen in patients who did not develop rejection or chronic graft injury.

The observance of selective clonal expansion with more dominant clones only in patients who develop both rejection and/or progressive chronic Ktx injury, suggests a biologically relevant, allo-antigen driven selection, persistence and expansion of certain clones over time, which accounts for the overall reduction in temporal diversity.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of detecting clonotypes comprising IGHV3-23 comprising the steps of:
   obtaining a sample from a subject with a kidney transplant; and
   assessing the abundance of selected clonotypes comprising IGHV3-23 sequences in the sample using BCR-Seq.

2. The method of claim 1, wherein
   the selected clonotypes comprising IGHV3-23 sequences are B cell receptors or immunoglobulins.

3. The method of claim 1, wherein
   the sample is a peripheral blood sample.

4. The method of claim 1, comprising the further step of administering an appropriate immunosuppressive treatment to the subject.

5. The method of claim 1, wherein the IGHV3-23 sequences comprise nucleic acid sequences or amino acid sequences.

6. The method of claim 1, wherein the IGHV3-23 sequences comprise B cell genomic DNA sequences or B cell RNA sequences.

7. The method of claim 4, wherein the immunosuppressive treatment is selected from the group consisting of glucocorticoids, calcineurin inhibitors, antimetabolite agents, rapamycin inhibitors, and polyclonal antilymphocyte antibodies.

* * * * *